United States Patent [19]

Gassman et al.

[11] 4,035,375

[45] July 12, 1977

[54] N-SUBSTITUTED AMINO PYRIDINES AND DERIVATIVES THEREOF

[75] Inventors: Paul G. Gassman; Gordon D. Gruetzmacher, both of Columbus, Ohio

[73] Assignee: The Ohio State University Research Foundation, Columbus, Ohio

[21] Appl. No.: 686,330

[22] Filed: May 14, 1976

Related U.S. Application Data

[62] Division of Ser. No. 553,602, Feb. 27, 1975, Pat. No. 3,985,756, which is a division of Ser. No. 327,294, Jan. 29, 1973, Pat. No. 3,894,034.

[51] Int. Cl.$^2$ .............. C07D 213/38; C07D 417/06
[52] U.S. Cl. ................. 260/294.8 G; 260/294.8 D; 260/294.8 E; 260/326.11 R; 260/326.12 R; 260/326.13 R; 260/315; 260/294.8 C; 260/465 E; 260/470; 260/551 S; 260/574; 260/575; 260/577
[58] Field of Search ............. 260/294.8 G, 294.8 E, 260/294.8 D

[56] References Cited
PUBLICATIONS

Kharasch, Organic Sulfur Compounds, vol. 1, Pergamon Press (1961).
Kharasch, Organic Sulfur Compounds, vol. II, Pergamon Press (1966).
Gassman et al., Tetrahedron Letters, No. 6, Pergamon Press, pp. 497–500, (Feb. 1972).

*Primary Examiner*—Alan L. Rotman
*Attorney, Agent, or Firm*—Gordon W. Hueschen

[57] ABSTRACT

Preparing ortho-substituted anilines by reacting an N-chloroaniline with a non-carbonylic di-hydrocarbon sulfide to form an azasulfonium chloride, reacting the azasulfonium chloride with a strong base to form an aniline substituted in the 2-position with a hydrocarbon-S-hydrocarbyl thio-ether group. The ortho-substituted thio-ether compounds can be reduced with a de-sulfurizing reducing agent such as Raney nickel or the like to form the orthoalkylated aniline. The analine may be an amino-pyridine. The azasulfonium salt and thio-ether intermediate products can be isolated and recovered. If desired, the thio-ether compounds can be reduced to form ortho-alkylated aniline products which are useful as intermediates for a wide variety of purposes, including their uses in making dyes, herbicides, and the like.

5 Claims, No Drawings

N-SUBSTITUTED AMINO PYRIDINES AND DERIVATIVES THEREOF

This is a division of Application Ser. No. 553,602, filed Feb. 27, 1975, now U.S. Pat. No. 3,985,756 issued Oct. 12, 1976 which is in turn a division of application Ser. No. 327,294, filed Jan. 29, 1973, now U.S. Pat. 3,894,034, issued July 8, 1975.

The following invention was made under a grant or award from the United States Department of Health, Education and Welfare.

FIELD OF THE INVENTION:

This invention relates to processes for otho-alkylating anilines. More particularly, this invention provides an improved process for preparing ortho-substituted anilines and ortho-substituted amino-pyridines.

Of the various methods available for the formation of carbon to carbon bonds to aromatic rings, termed "alkylation" herein, the classical Friedel-Crafts reaction is undoubtedly the best known and the most widely used. C. Friedel and J. M. Crafts, *Compt. Rend.*, 84, 1392, 1450 (1877). See also G. A. Olah, "Friedel-Crafts and Related Reactions", Interscience, New York (1963–1965). However, in the alkylation of some aromatic molecules, the Friedel-Crafts reaction is not as stereo-specific as desired. There continues to be a need for an improved process for preparing certain isomerically pure poly-substituted aromatic compounds.

Part of the subject matter claimed herein has already been published in *Tetrahedron Letters*, No. 6, pp. 497–500 (1972). The prior art is cited in the bibliography of that publication. The closest prior art references of which we are aware are: a) P. Claus and W. Vycudilik, *Monatsh. Chem.*, 101, 396 (1970), wherein Claus et al. reacted an aniline with a dimethylsulfoxide to form sulfiliminic compounds, not azasulfonium salt compounds, and b) P. Claus, W. Vycudilik, and W. Rieder, *Monatsh. Chem.*, 102, 1571 (1971), wherein these sulfiliminic compounds are themally rearranged to hydrocarbon-S-hydrocarbon aromatic amine thio-ethers. Another paper published simultaneously with our own abovementioned paper is that of Prof. C. R. Johnson et al., *Tetrahedron Letters*, No. 6, 501–504 (1972).

SUMMARY OF THE INVENTION:

We have discovered a process for orthoalkylating a primary or secondary aromatic amine by (a) reacting the N-chloro-aromatic amine with an organic sulfide ether under substantially anhydrous conditions to form the azasulfonium salt; (b) reacting the azasulfonium salt with a strong base under substantially anhydrous conditions to form the ortho-hydrocarbon-S-hydrocarbon aromatic amine thio-ether. If desired, the thio-ether can be reduced to form the ortho-hydrocarbon aromatic amine. This reaction is applicable to both anilines and aminopyridines. Some of these thio-ether compounds are new and are claimed herein as such. The process can be conducted in one reaction vessel, without separation of the intermediate reaction products up to the isolation of the thio-ether. However, the azasulfonium salt and thio-ether compound intermediates can be isolated and separated to a separate reaction vessel, if desired.

OBJECTS OF THE INVENTION

It is an object of this invention to provide a process which permits the stereospecific ortho-alkylation of primary and secondary aromatic amines.

It is another object of this invention to provide a simple process for preparing anilines and aminopyridines having carbon-to-carbon bonded substituents in the position ortho to the amine moiety which can be run in a short time with simple equipment and without isolation of intermediates.

It is a further object of this invention to provide some new ortho-substituted thio-ether-containing amino-pyridines as new compounds which are useful as intermediates in the process described herein for making ortho-alkylated amino-pyridine compounds. Other objects will become apparent to the artisan.

DETAILED DESCRIPTION OF THE INVENTION

More specifically, this invention provides an improved aromatic amine alkylation process and some new intermediate chemical compounds which are useful in making ortho-substituted aromatic amines.

According to the process of this invention, the primary or secondary selected aniline or amino-pyridine starting material, both being referred to hereinafter as an "aniline", is first reacted with a source of positive halogen to prepare the N-haloaniline. Many sources of positive halogen are known and can be used to prepare N-halo-anilines. Examples of positive halogen sources for this reaction include t-butyl hypochlorite, N-chlorosuccinimide, calcium hypochlorite, sodium hypochlorite, sodium hypobromite, and the like. The N-chloro anilines are preferred for reasons of availability of reactants to make them and cost of materials, but other positive halogen compounds can be used to make useful N-halo-anilines for use in this process.

The essential features of the process comprise: (a) reacting under substantially anhydrous conditions in an organic diluent an N-halo-aniline of the formula:

wherein

R is hydrogen or a hydrocarbon radical free of aliphatic unsaturation containing from 1 to 8 carbon atoms;

X is —CH= or —N= and is in a position ortho, meta, or para relative to the

group; each of Y and Z is hydrogen or a noninterfering substituent such as halogen (chlorine, bromine, fluorine, iodine), nitro, cyano, amino (—NH$_2$), lower alkylamino, lower alkyl, lower alkyloxy, lower acyloxy, or a carbonyloxy-lower alkyl, or a carbonyloxy-phenyl; and A denotes chlorine or bromine, but is preferably chlorine; with a non-carbonyl organic sulfide of the formula:

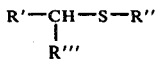

wherein
R' is hydrogen, lower alkyl or phenyl;
R'', taken separately, is lower alkyl or phenyl;
R''', taken separately, is hydrogen or lower alkyl or phenyl; and
R'' and R''', when taken together with the

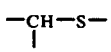

denote a ring containing 3 to 5 methylene carbon atoms, to form an azasulfonium salt of the formula:

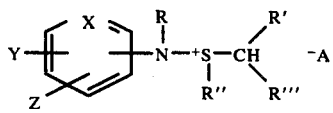

wherein X, Y, Z, R, R', R'' and R''' are as defined above and ⁻A is a halogen ion, which halogen ion can be replaced, if desired, by another ion by reaction with a silver salt thereof, e.g., nitro, trifluoroacetate, or the like;

b. reacting the azasulfonium salt (III) with a substantially anhydrous base, with a pKa greater than 6, to effect rearrangement and to form a thio-ether compound of the formula:

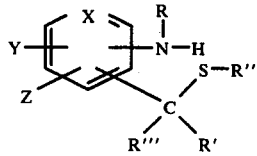

wherein X, Y, Z, R, R', R'' and R''' are as defined above and the thio-ether group (i.e., the hydrocarbon-S-hydrocarbyl thio-ether group) is ortho to —N(R)H. These thio-ether compounds can be recovered, packaged and shipped as such. They are particularly useful for making ortho-substituted anilines and amino-pyridines by reacting the thio-ether compound IV with a de-sulfurizing reducing agent to form the ortho-substituted aniline product of the formula:

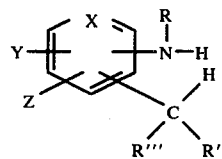

wherein X, Y, Z, R, R' and R''' are as defined above, except that where R'' and R''' had been taken together with the

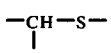

moiety to form a ring, the R''' group now includes the tri-, tetra- or penta-methylene chain therefrom, and the —CHR'R''' is ortho to the anilino nitrogen.

As used herein, the term "lower alkyl" means a $C_1$ to $C_6$ alkyl radical, e.g., methyl, ethyl, propyl, isopropyl, n-butyl, isobutyl, tert.-butyl, n-pentyl, neo-pentyl, n-hexyl, and the like. The term "lower alkyloxy" denotes a $C_1$ to $C_6$ alkyl-O- group wherein the $C_1$ to $C_6$ alkyl group is exemplified as above. The term "lower acyloxy" denotes a formyloxy and a $C_1$ to

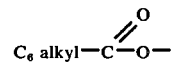

group wherein the $C_1$ to $C_6$ alkyl is exemplified as above.

The aniline and aminopyridine compunds which can be used as starting materials in this process are those which have a free, unsubstituted position on the aromatic ring ortho to the amino group. Such compounds are known compounds, many of them being articles of commerce. Many of them are described in publications such as "Chem Sources", Directories Publishing Co., Flemington, N.J. 08822 (1972). Examples include aniline, the chloroanilines such as 3-chloroaniline, 4-chloroaniline, 3,4-dichloroaniline, the toluidines such as 2-methylaniline, 3-methylaniline, 4-methylaniline, 2-ethylaniline, 3-ethylaniline, 4-ethylaniline, 3-propylaniline, 4-hexylaniline, 3-chloro-4-methylaniline, the lower alkyloxy substituted anilines such as 3-methoxyaniline, 4-methoxyaniline, 4-ethoxyaniline, the 3- and 4-carbonyloxy-lower alkyl anilines, such as benzocaine (4-ethoxycarbonylaniline), 4-phenoxy-carbonylaniline, 3-methoxycarbonylaniline, 3-ethoxycarbonylaniline, the nitro anilines such as 3-nitroaniline, 4-nitroaniline, and amino-pyridines such as 2-aminopyridine, 4-methyl-2-aminopyridine, 4-ethyl-2-aminopyridine, 4-hexyl-2-aminopyridine, 4-methoxy-2-aminopyridine, 4-hexyloxy-2-aminopyridine,
3-aminopyridine, 4-aminopyridine, 3-bromo-4-aminopyridine, 3-iodo-4-aminopyridine, 4-ethoxycarbonyl-2-aminopyridine, 4-chloro-2-aminopyridines, and the like. Secondary anilines and aminopyridines, which may be used, are those having a $C_1$ and $C_8$-hydrocarbon group bonded to the amino nitrogen and include the $C_1$ to $C_8$-alkyl, such as the N-methyl, N-ethyl, N-butyl, N-tert.-butyl, N-octyl, N-phenyl, N-tolyl, N-xylyl, N-cycloalkyl such as N-cyclopropyl, N-cyclobutyl, N-cyclopentyl, N-cyclohexyl, and N-cyclooctyl anilines and 2-aminopyridines, and such compounds substituted on ring carbon atoms thereof with halogen, nitro, cyano, amino, lower alkyl, lower alkyloxy, lower alkyl-C(0)0-[namely, lower alkanoyloxy], carbonyloxy-lower alkyl or carbonyloxyphenyl groups as described and exemplified above.

Examples of the non-carbonylic di-organo sulfides which can be used to react with the N-haloaniline in the process of this invention include the di-lower alkyl sulfides having at least one hydrogen on a carbon atom bonded to the sulfur atom, such as dimethylsulfide, diethylsulfide, dipropylsulfide, dihexylsulfide, the mixed alkyl sulfides, such as methyl ethyl sulfide, ethyl propyl sulfide, methyl tert-butyl sulfide, the $C_3$ to $C_5$ saturated cyclic sulfides such as trimethylene sulfide, tetrahydrothiophene, pentamethylene sulfide, the lower-alkyl phenyl sulfides such as methyl phenyl sulfide, ethyl phenyl sulfide, isopropyl phenyl sulfide, hexyl phenyl sulfide, benzyl phenyl sulfide, loweralkyl benzyl sulfides, such as methyl benzyl sulfide, ethyl benzyl sulfide, propyl benzyl sulfide, butyl benzyl sulfide, hexyl benzyl sulfide, and the like.

The reaction of this process between the N-haloaniline and the non-carbonyl di-organo sulfide, and between the azasulfonium salt and the strong base can be conducted in a wide variety of inert organic solvents and diluents.

Solvents as extreme in polarity as toluene and methanol have been used. Methylene chloride has been most commonly used. The reactions can be run over a broad temperature range, ranging from dry-ice/acetone temperatures (about −78° C.) to about 100° C. or more, but the preferred temperature with any particular set of reactants will depend upon the substitutents, if any, on the aromatic ring since these effect the stability of intermediate N-haloanilines. Preferably the reactions are run at temperatures between about −78° C. and room temperature to insure control over the reaction of the most active reactants with simple equipment. However, with some reactants, the reactions can be run at higher temperatures, for example up to about 100° C. These azasulfonium salt and thio-ether formation steps of the process are conducted under substantially anhydrous conditions; that is, a reasonable degree of care is taken to avoid the introduction of water into the reaction mixtures, although the introduction of small, incidental amounts of water introduced with solvents or reactants is not substantially detrimental to the process. After the formation of the azasulfonium salt intermediate the reaction temperature becomes less critical.

The base which is reacted with the azasulfonium salt (III) to effect rearrangement and to form the thio-ether compound (IV) can be any base which will cause formation of an ylid intermediate which will undergo a Sommelet-Hauser type of rearrangement, and effect hydrogen transfer to produce the thio-ether compound IV. Bases which can be used are those which have a pKa of greater than about 6 and include the alkanolic alkali metal hydroxides such as methanolic sodium hydroxide, potassium hydroxide, lithium hydroxide, and calcium hydroxide, as well as sodium methoxide, potassium methoxide, sodium and potassium ethoxides, potassium or sodium carbonate, and organic bases, such as the lower-alkylamines such as diethylamine, ethylamine, triethylamine, tributylamine, pyridine, the lutidines, and the like. Treatment of the azasulfonium salt with the base at any convenient temperature such as room temperature, results in rapid conversion of the azasulfonium salt through its intermediates to the respective thio-ether aniline products. The thio-ether compound (IV) can be isolated, if desired, by known procedures. However, the thio-ether compounds (IV) find particular utility in the process of this invention to prepare the ortho-alkylated aniline products by ready conversion to those products by catalytic reduction procedures. For example, the thio-ether compound can be treated with W-2 Raney nickel or other reducing agent to remove the sulfur and form the orthosubstituted product.

In a typical procedure, one equivalent, about 0.1 mole, of tert.-butyl hypochlorite in 10 ml. of methylene chloride is added to a vigorously stirred solution of one equivalent, about 0.1 mole, of aniline in 400 ml. of methylene chloride at −65° C. The reaction mixture is stirred for about 25 minutes to insure formation of the N-chloroaniline. The reaction mixture is stirred for about 25 minutes and 3 equivalents of dimethyl sulfide is added at about −65° C. The reaction mixture is stirred for 40 minutes to form the azasulfonium salt intermediate (III), and then a solution of 1.2 equivalents of sodium methoxide in 50 ml. of methanol is added at about −65° C. The reaction mixture is stirred for about one hour at −65° C. and then warmed to room temperature to form the 2-thiomethoxymethylaniline (which can also be named as a 2-methyl-thiomethylaniline) product of the process. If desired, the 2-thiomethoxymethylaniline can be reduced to the 2-methylaniline by treatment with Raney nickel at room temperature. In those cases when Raney desulfurization is done, the yields of the resultant o-toluidine derivatives range from 60 to 88 percent for the reduction. The specificity of the ortho substitution represents a distinct advantage over the Friedel-Crafts reaction.

Products produced by the process of this invention can be used for a wide variety of purposes. Ortho-alkylated anilines can be used as intermediates in making dyes, as reactants for making photoconductive layers for use in color photographic processes, or as complexes in color photography. Ortho-alkylated anilines are also useful as intermediates in preparing pesticides and herbicides in agricultural chemical products. For example, 2',6'-diethyl-N-methoxymethyl-2-chlorocetanilide and similar compounds which can be prepared from the ortho-alkylated aniline products according to the process of the present invention are effective fungicides, week killers, insecticides, nematocides, algicides and bacteriocides. *Chem. Abstr.*, 58, 8074d (1963). See also U.S. Pat. No. 3,551,132, South African Pat. No. 68 07 934 (1968), *Chem. Abstr.* 72, 55033e (1970), as well as references to the uses of ortho-alkylated aniline derivatives at *Chem. Abstr.*, 75, 4407, 34326z, 87362q, 97,569b, 108,876c (1971). Synergistic use of a combination of ortho-alkylated aniline derivatives is disclosed in French Pat. No. 2,040,726 (1971), *Chem. Abstr.* 75, 117,430e (1971). In addition, compounds produced by the process of this invention can be converted to Schiff bases for use as weed killers, or to N-phenylcarbamates for use as pesticides, U.S. Pat. No. 3,567,776, or to 4-(methylcarbamoyl)carbanilates for use as systemic insecticides and nematocides, U.S. Pat. No. 3,546,343. The products of this invention can also be used as intermediates in preparing α-cyanoethyl-N-phenylcarbamates which have fungicide utility, U.S. Pat. No. 3,557,183. Ortho-akylated phenyl thioureas, which can be prepared from compounds of the invention are effective as molluscides, U.S. Pat. No. 3,546,344.

The ortho-alkylated anilines and aminopyridines have a wide variety of other uses. They can be used as accelerators for polyepoxide resins, in hardening compositions to increase the hardness of enamel coatings, and in compositions to lower the temperature of drying in an electro-insulating enamel, as de-icing additives in gasoline, as plasticizers for poly(vinylchloride), as intermediate to make acetanilides which exhibit analgesic activity and as corrosion inhibitors in a hydrochloric acid solution to prevent steel corrosion.

The invention is further exemplified by the following detailed Examples and Preparations which are given by way of illustration only.

EXAMPLE 1

Preparation of N-t-butylanilino dimethyl sulfonium chloride

Ref.: P. Haberfield and D. Paul, *J.Am.Chem.Soc.*, 87, 5502, (1965) — (for preparation of N-chloro amine).

In a suitable reaction vessel, 7.96 grams (0.0534 mole) of N-t-butylaniline was placed in a three-necked flask with 150 ml. of pentane under a nitrogen atmosphere. The solution was cooled to $-10°$ C.; 63.4 grams (8.3 equivalent) of calcium hypochlorite was added; and the mixture stirred for one hour. The excess Ca(OCl)$_2$ was removed by filtration and the solution concentrated by rotatory evaporation.

The N-chloramine formed was used without further purification. The N-chloro-N-t-butylaniline was placed in a three-necked flask under N$_2$ (nitrogen) and the flask cooled to $-10°$ C; and 40 ml of dimethyl sulfide was slowly added (about five minutes) to the N-chloramine. After five minutes the reaction flask was removed from the bath, allowed to come to room temperature, and stirred for 3½ hours. The white precipitate formed was collected by filtration to yield 10.39 grams (0.0423 mole) of N-t-butylanilino dimethyl sulfonium chloride for an 80% yield.

An analytical sample was prepared by low temperatures recrystallization three times from methylene chloride ethyl ether. M.p 147°–148° C.

|  | C | H | N | S |
|---|---|---|---|---|
| Calculated | 58.63 | 8.20 | 5.70 | 13.04 |
| Found | 58.63 | 8.25 | 5.67 | 12.98 |

IR: 2950, 1525, 1200, 995, 790, 725 cm$^{-1}$ KBr pellet.
NMR: (in CDCl$_3$ and TMS).

| 5H- | multiplet | 2.30–2.85T |
|---|---|---|
| 6H- | singlet | 6.72T |
| 9H- | singlet | 8.56T |

EXAMPLE 2

Preparation of N-t-butyl-p-toluidino dimethyl sulfonium chloride

In a suitable reaction vessel, 10.00 grams (0.0578 mole) of N-t-butyl-p-toluidine was placed in 250 ml of pentane in a three-necked, round bottom flask in a N$_2$ atmosphere. This solution was cooled to $-10°$ C., and 82 grams (about 10 equivalents) of Ca(OCl)$_2$ was added. After the reaction was stirred for 1 hour at $-10°$ C., the excess Ca(OCl)$_2$ was filtered off, and the solution concentrated on the rotatory evaporator. The N-chloramine prepared was used in the next step without further purification.

The chloramine was placed in a three-necked, round bottom flask, cooled to $-10°$ C. under N$_2$, and 100 ml of dimethyl sulfide was added slowly (about 5 minutes) while stirring; the flask was kept in the cooling bath for 5 minutes more after completion of the addition of sulfide. The mixture was stirred at room temperature for 4 hours. The salt formed was collected under an anhydrous atmosphere to give 11.96 grams (0.0460 mole of N-t-butyl-p-toluidino dimethyl sulfonium chloride for a 76.5% yield. (This salt is extremely hygroscopic and must be maintained under an anhydrous atmosphere.)

An analytical sample was prepared by low temperature recrystallization three times from CHCl$_3$ ether. Between recrystallizations the salt was dissolved in CHCl$_3$ and stirred over 3A molecular sieve. M.p. 153°–154° C.

|  | C | H | N | S | Cl |
|---|---|---|---|---|---|
| Calculated | 60.09 | 8.53 | 5.39 | 12.34 | 13.64 |
| Found | 59.80 | 8.37 | 5.43 | 12.04 | 13.53 |

IR: (as a solid pulverized and compressed into a KBr pellet) 2940, 1500, 1375, 1180, 985, 745 cm$^{-1}$
NMR: (in CDCl$_3$ and TMS)

| 4H- | multiplet | 2.45–2.88T |
|---|---|---|
| 6H- | singlet | 6.72T |
| 3H- | singlet | 7.53 |
| 9H- | singlet | 8.58 |

EXAMPLE 3

Preparation of 4-chloro-N-t-butyl-anilino dimethyl sulfonium chloride

In a suitable reaction vessel, 10.00 grams (0.0546 mole) of p-chloro-N-t-butyl aniline was placed in a three-necked, round bottom flask under N$_2$ with 250 ml of pentane. 78 grams (10 equivalents) of freshly ground calcium hypochlorite was added and the solution was stirred for three hours at room temperature. After the reaction time, the excess Ca(OCl)$_2$ was filtered off, the pentane removed by rotatory evaporation, and the N-chloramine used in the next step without further purification.

The chloramine was placed in a flask under nitrogen, 100 ml. of di-methyl sulfide added over a period of about 15 minutes, and the solution stirred for six hours at room temperature. The named product salt formed, was collected in the dry box and dried. The yield of the salt was 9.04 grams for a 59% yield. (0.0322 mole)

IR: (as KBr pellet) 2900, 1480, 1180, 1085, 725, 705 cm$^{-1}$

NMR: (In CDCl$_3$ and TMS)

| 4H- | multiplet | 2.02–2.83T |
|---|---|---|
| 6H- | singlet | 6.75T |
| 9H- | singlet | 8.62T |

EXAMPLE 4

Preparation of N-t-butyl anilino dimethyl sulfonium trifluoroacetate

In a suitable reaction vessel, 5.40 grams (0.0220 mole) of N-t-butyl anilino dimethyl sulfonium chloride was dissolved in 50 ml of dry methanol; 4.86 grams (0.0220 mole) of silver trifluoroacetate was dissolved in 50 ml of dry CH$_3$OH and added to the sulfonium salt solution over a period of about 3 minutes. Upon commencement of the addition of the trifluoroacetate solution, a white precipitate formed. After 2 hours at room temperature, the AgCl was filtered off, and CH$_3$OH removed by rotatory evaporation. This procedure yielded a reddish-brown oil which was triturated with dry ether to yield a white salt. This salt was dried to yield 5.43 grams (0.0168 mole) of N-t-butyl anilino dimethyl sulfonium trifluoroacetate for a 76% yield.

Three low temperature recrystallizations from methylene chloride ethyl ether gave an analytical sample, m.p. 149°–150° C.

|  | C | H | N | S |
|---|---|---|---|---|
| Calculated | 52.00 | 6.23 | 4.33 | 9.92 |
| Found | 51.82 | 6.24 | 4.26 | 10.19 |

IR: (as a KBr pellet) 3000, 1690, 1190, 1115, 975, 820,

| | |
|---|---|
| 715, 705 cm$^{-1}$ | |
| NMR: (in CDCl$_3$ and TMS) | |
| 5H- multiplet | 2.36–2.89T |
| 6H- singlet | 6.91T |
| 9H- singlet | 8.61T |

EXAMPLE 5

Sodium methoxide rearrangement of N-t-butyl anilino dimethyl sulfonium chloride

In a suitable reaction vessel, 1.00 gram (4.06 mole) of N-t-butyl anilino dimethyl sulfonium chloride was dissolved in 5 ml. of dry methanol and cooled to 0° C; 0.5 grams (5.35 equivalents) of sodium metal was placed in 15 ml. of dry methanol and cooled to 0° C. The methoxide solution was added to the sulfonium salt solution over a period of about 10 minutes at 0° C. After the addition of the sodium methoxide was completed, the ice bath was removed and the solution allowed to stir at room temperature for 2 hours. Then 10 ml. of water was added to the reaction mixture and the mixture was extracted three times with 20 ml. of ether. The organic layer was dried with saturated NaCl solution and stirred over MgSO$_4$. The ether was removed by rotatory evaporation to yield a yellow oil. Molecular distillation gave 0.81 gram (3.87 mole) of N-t-butyl-2-(thiomethoxymethyl)aniline for a 95% yield.

$N_D^{26.4}$ 1.5532

| | C | H | N | S |
|---|---|---|---|---|
| Calculated | 68.85 | 9.15 | 6.69 | 15.31 |
| Found | 68.86 | 9.06 | 6.58 | 15.07 |

IR: (as a neat liquid on NaCl plates) 3050, 1690, 1480, 1240, 790
NMR: (in CCl$_4$ and TMS)

| | |
|---|---|
| 4H- multiplet | 2.84–3.64T |
| 1H- broad singlet | 5.56–5.85T |
| 2H- singlet | 6.46T |
| 3H- singlet | 8.15T |
| 9H- singlet | 8.64T |

EXAMPLE 6

Sodium methoxide rearrangement of N-t-butyl-p-toluidino dimethyl sulfonium chloride In a suitable reaction vessel, 1.00 gram (3.61 moles) of N-t-butyl-p-toluidine dimethyl sulfonium chloride was dissolved in 0.5 ml. of dry methanol; 0.5 gram (6 equivalents) of sodium was placed in 15 ml. of dry CH$_3$OH. Both solutions were cooled to 0° C. and the sodium methoxide solution added over a period of about 10 minutes to the sulfonium salt solution. After the addition of the sodium methoxide solution, the ice bath was removed and the solution stirred for four hours at room temperature. At this time 15 ml. of water was added to the reaction mixture and this solution extracted three times with 25 ml. of ether. The organic layer was dried with saturated NaCl solution and stirred over MgSO$_4$. Rotatory evaporation removed the ether to yield a light yellow oil. Molecular distillation of the oil yielded 0.75 gram (3.36 moles) of N-t-butyl-5-methyl-2-(thiomethoxymethyl)aniline for a 92% yield.

$N_D^{26.8}$ 1.5473

| | C | H | N | S |
|---|---|---|---|---|
| Calculated | 69.70 | 9.48 | 6.27 | 14.35 |
| Found | 70.00 | 9.67 | 6.23 | 14.11 |

IR: (as a neat liquid on NaCl) 3000, 1490, 1350, 1210, 805 cm$^{-1}$
NMR: (in CCl$_4$ and 1% TMS)

| | |
|---|---|
| 3H- multiplet | 3.03–3.42T |
| 1H- singlet (broad) | 5.79–5.98T |
| 2H- singlet | 6.52T |
| 3H- singlet | 7.87T |
| 3H- singlet | 8.20T |
| 9H- singlet | 8.69T |

EXAMPLE 7

Sodium methoxide rearrangement of 4-chloro-N-t-butyl anilino dimethyl sulfonium chloride In an anhydrous atmosphere, 1.47 grams (5.25 moles) of 4-chloro-N-t-butyl aniline dimethyl sulfonium chloride was placed in a tared three-necked flask. The flask was removed from the dry box, nitrogen passed through the flask, and 25 ml. of dry methanol added. The flask was cooled to 0° C., 0.40 gram (1.4 equivalents) of sodium methoxide was dissolved in 25 ml. of methanol and cooled to 0° C. The sodium methoxide was added over a period of about 15 minutes, after which time the reaction mixture was allowed to stir at room temperature for 2 hours. 25 ml. of water was added and this solution was extracted three times with 25 ml. of ether. The organic layer was dried with saturated sodium chloride solution and stirred over magnesium sulfate. Removal of the ether by rotatory evaporation produced a light yellow oil. Molecular distillation of the oil gave 1.16 grams (4.76 mmole) of N-t-butyl-5-chloro-2-(thiomethoxymethyl)aniline for a 90% yield.

$N_D^{24.2}$ 1.5649

| | C | H | N | S | Cl |
|---|---|---|---|---|---|
| Calculated | 59.12 | 7.44 | 5.75 | 13.15 | 14.54 |
| Found | | | | | |

IR: (as a neat liquid in NaCl plate) 3000, 1510, 1460, 1210, 805 cm$^{-1}$
NMR: (in CDCl$_3$ and TMS)

| | |
|---|---|
| 3H- multiplet | 2.69–3.43T |
| 1H- singlet (broad) | 5.85–5.97T |
| 2H- singlet | 6.40T |
| 3H- singlet | 8.03T |
| 9H- singlet | 8.61T |

EXAMPLE 8

Sodium methoxide rearrangement of N-t-butyl anilino dimethyl sulfonium trifluoroacetate In a suitable reaction vessel, 1.00 gram (3.09 moles) of N-t-butyl anilino dimethyl sulfonium trifluoroacetate was dissolved in 10 ml. of dry methanol and cooled at 0° C., while 0.5 gram sodium (7.0 equivalents) was placed in 15 ml. of dry methanol and also cooled to 0° C. The sodium methoxide was added over a period of about 10 minutes, after which time the ice bath was removed. The reaction was stirred for 1½ hours at room temperature. The methanolic solution was taken up in 20 ml. of water, and this solution was extracted three times with 50 ml. of ether. The organic layer was dried with saturated sodium chloride and stirred over magnesium sulfate. Removal of the ether by rotatory evaporation yielded a light yellow oil. Molecular distillation of the oil produced 0.54 gram (2.58 moles) of N-t-butyl-2-(thiomethoxymethyl)aniline for an 83% yield.

EXAMPLE 9

Preparation of 4-methyl-2-(methylthiomethyl) aniline.

In a suitable reaction vessel, a solution of 11.50 grams (0.1075 mole) of p-toluidine in 400 ml. methylene chloride was vigorously stirred and cooled to −65° C. under nitrogen. To this solution was added dropwise 11.68 grams (0.1075 mole) of tert.-butyl hypochlorite in 20 ml. of methylene chloride also at −65° C. to form the N-chlorotoluidine. After the addition was complete, the solution was stirred for 15 minutes. The addition funnel was rinsed with 40 ml. of methylene chloride and 25 ml. (ca. 3 equivalents) of dimethyl sulfide were placed in it and cooled to −65° C. The dimethyl sulfide was added dropwise to N-chloro-p-toluidine solution and stirred for 3½ hours at −65° C. to form the azasulfonium chloride salt. In 50 ml. of methanol, 7.0 grams (0.1290 mole, 1.2 equivalents) of sodium methoxide was placed in the funnel, cooled to −65° C., and added quickly to the reaction mixture. This solution was allowed to stir for one hour at −65° C. after which time the dry ice/acetone bath was removed and the reaction mixture allowed to come to room temperature. In order to remove the inorganic salts, 150 ml. of water were added to the reaction, the layers were separated, the aqueous phase was washed twice with 100 ml. of methylene chloride. The combined organic layers were dried with anhydrous magnesium sulfate and filtered. The solvents were removed in vacuo to yield a red oil. This oil was fractionally distilled to yield 3.04 grams (0.028 mole, 26%, b.p. 85°–90° C. at 15 mm) of p-toluidine and 7.50 grams (b.p. 90°–92.5° C. at 0.03 mm Hg) of 4-methyl-2-(thiomethoxymethyl)aniline which was recrystallized from pentane to yield 7.28 grams (0.044 mole, 40%, m.p. 46.5°–47° C.). The yield of 4-methyl-2(thiomethoxymethyl)aniline based on unrecovered p-toluidine is 55%.

EXAMPLE 10

Preparation of 2-chloro-6(thiomethoxymethyl)aniline

The procedure was identical with that used in the preparation of 3- and 5-chloro-2(thiomethoxymethyl)aniline.

In this manner 2-chloro-6(thiomethoxymethyl)aniline was synthesized from o-chloroaniline in 26% (5.25 grams, 0.029 mole) yield: $N_D^{23.7}$ 1.6160 (lit $N_D$ 1.6730). Also recovered was 8.68 grams (0.068 mole) of o-chloroaniline. The yield based on unrecovered starting material is 72%.

EXAMPLE 11

Preparation of 4-methoxy-2(thiomethoxymethyl)aniline

In a suitable reaction vessel, 150 ml. of methylene chloride were placed. 4.65 ml. (3 equivalents) of dimethyl sulfide were added and cooled to −78° C. under nitrogen. In a jacketed constant pressure addition funnel 2.17 grams (0.02 mole) of tert.-butyl hypochlorite in 10 ml. of methylene chloride was cooled to −78° C. and added dropwise to the dimethyl sulfide solution. This reaction mixture was stirred for 10 minutes. In a non-jacketed addition funnel were placed 2.46 grams (0.02 mole) of p-anisidine in 20 ml. of methylene chloride which was added dropwise to the reaction mixture. The reaction was stirred for 2 hours at −78° C. In 25 ml. of absolute methanol was dissolved 2.28 grams (2 equivalents) of sodium methoxide; this solution was added dropwise to the reaction mixture which was stirred for 15 minutes at −78° C. At this time the dry ice/acetone bath was removed, and the reaction was allowed to come to room temperature. The reaction was quenched with 50 ml. of water; the layers were separated; the aqueous phase was extracted two times with 50 ml. of methylene chloride. The combined organic extracts were dried over anhydrous magnesium sulfate, filtered, and concentrated to yield a dark oil. This oil was distilled to give a yellow oil (b.p. 80°–120° C. at 0.1 mm) which solidified. Preparative gas chromatograph on a 10% Carbowax 20M-KOH on 60–80 "Chromosorb W" column at 190° C. with a flow rate of 200 ml/min was used to separate product from starting material. The first compound eluted was p-anisidine (0.56 gram, 4.6mmols), the second compound eluted was 4-methoxy-2(methylthiomethyl)aniline (82 mg, 0.45 mmole, 2.2%, 2.9% based on recovered starting material):

$N_D^{24.4}$ 1.5965; IR (neat) 2.90, 3.38, 6.64, 8.03, 9.60, and 12.35μ

NMR: (CCl$_4$) 8.06 (3H, S), 6.46 (2H, S), 6.32 (3H, S), 6.30 (2H, broad singlet), 3.48 (3H, S).

Anal. Exact theoretical weight, calculated for $C_9H_{13}NOS$: 183.0717. Found 183.0720.

"Chromosorb W" is a flux calcined diatonite support preparation from the production of Johns Manville Celite filter aid such as Celite 545. See also H. M. McNair et al. "Basic Gas Chromatography" 5th ed., Varian-Aerograph, Walnut Creek, California, p. 50 (1969).

EXAMPLE 12

Preparation of 4-carboethoxy-2-(thiomethoxymethyl) aniline

A solution of 16.52 grams (0.10 mole) of benzocaine in 400 organic layers ml. of methylene chloride was vigorously stirred with a Herschberg stirrer and cooled to −78° C. under nitrogen. To this solution were added dropwise 10.85 grams (0.10 mole) of tert.-butyl hypochlorite in 10 ml. of methylene chloride to form the N-chlorobenzocaine. After the reaction mixture had stirred for two hours, 25 ml. (3 equivalents) of dimethyl sulfide were added to the solution; this solution was stirred for 18 hours. A solution of 6.48 grams (1.2 equivalents) of sodium methoxide in 50 ml. methanol were added to the reaction mixture; this resultant solution was stirred for one hour at −78° C. at which time the dry ice/acetone bath was removed and the reaction allowed to come to room temperature. The inorganic salts formed were hydrolyzed by the addition of 100 ml. of water, the layers separated, and the aqueous phase washed with two 150-ml. portions of methylene chloride. The combined organiclayers were dried over anhydrous magnesium sulfate, filtered, and the solvents evaporated to produce a dark red oil which solidified upon standing. This red solid was refluxed in 400 ml. of toluene with 25 ml. of triethyl amine for 24 hours. The solvent was removed by rotary evaporation to produce again a red oil which solidified upon standing. The solid was recrystallized in two crops from absolute alcohol to yield 14.70 grams (0.065 mole, 65%) of 4-carboethoxy-2-(thiomethoxymethyl)aniline, m.p. 83°–84.5° C. An analytical sample was prepared by recrystallizing a small portion twice from pentane-ether, m.p. 84.5°–85.5° C. IR (KBr) 2.95, 3.32, 5.93, 6.13, 6.25, 7.81, 8.37, 9.75, 12.96, μ; NMR (CDCl$_3$)tau 8.66 (3H, t), 8.04 (3H, s), 6.33 (2H, s), 5.68 (2H, q), 5.60 (2H, broad singlet), 2.78 (3H, m).

Anal. Calculated for $C_{11}H_{15}NO_2S$: C, 58.64; H, 6.71; N, 6.23; O, 14.20; S, 14.23. Found: C, 58.66; H, 6.66; N, 6.15.

EXAMPLE 13

W-2 Raney Nickel Preparation for Use

The W-2 Raney Nickel used in these experiments was obtained from W. R. Grace & Co., Raney Catalyst Division, South Pittsburg, Tennessee, as No. 28 Raney Active Nickel Catalyst in Water. A portion of this was placed in a beaker and washed with distilled water until neutral to pH paper and then several more times with distilled water, three times with 95% ethanol, and three times with absolute ethanol. The catalyst under absolute ethanol was stored in brown bottles until use.

EXAMPLE 13B

Preparation of o-toluidine

To a vigorously stirred solution of 2.50 grams (0.0163 mole) of 2-methylthiomethylaniline in 100 ml. absolute ethanol were added ca. 30 grams (10 level teaspoons) of W-2 Raney nickel. This solution was stirred for 30 minutes at room temperature. The Raney nickel was removed by filtration and washed five times with 100-ml. portions of absolute ethanol. The ethanol was removed at reduced pressure. The resultant residue was taken up in 200 ml. of methylene chloride, dried over magnesium sulfate. The drying agent was removed by filtration, and the solution concentrated on the rotary evaporator to yield a clear oil. Distillation of this oil gave 1.10 grams (0.0103 mole) of o-toluidine; $N_D^{22.8}$ 1.5680 (lit $^1N_D^{20}$ 1.5688); for a 63% yield. The o-toluidine produced was identical in all respects to an authentic sample.

[1]H. G. Tanner & P. A. Lasselle, J.Am.Chem.Soc., 48, 2165 (1926).

EXAMPLE 14

Preparation of 2-n-Butylaniline 2-n-butylaniline was produced from 2-(2-tetrahydrothienyl) aniline in 62% yield in a manner analogous to the procedure used to prepare o-toluidine in Example 13. The 2-n-butylaniline gave spectral data, NMR and IR, consistent with the structure and had the following index of refraction:

$N_D^{23.4}$ 1.5362.

EXAMPLE 15

Preparation of 4-carboethoxy-2-methyl aniline

To a vigorously stirred solution of 3.67 grams (0.0163 mole) of 4-carboethoxy-2-(thiomethoxymethyl)aniline in 100 ml. of absolute ethanol was added ca. 30 grams (10 teaspoons) of W-2 Raney Nickel. This mixture was stirred for 30 minutes at room temperature. The Raney Nickel was removed by filtration, washed twice with 100 ml. portions of absolute ethanol and twice with 100-ml. portions of methylene chloride. The combined washings were concentrated at reduced pressure to leave a clear oil. The oil was taken up in 100-ml. of methylene chloride and dried with anhydrous magnesium sulfate. The magnesium sulfate was removed by filtration and the solution concentrated at reduced pressure to give a clear oil which solidified upon standing. This procedure gave 2.66 grams (0.0143 mole, 88%) of 4-carboethoxy-2-methyl aniline, m.p. 76°–77° C.

EXAMPLE 16

Preparation of 2,6-xylidine 2,6-Xylidine was produced from 2-methyl-6-(thiomethoxymethyl)-aniline in 66% yield in a fashion analogous to the procedure used to prepare 4-carboethoxy-2-methyl aniline in Example 15.

$N_D^{24.4}$ 1.5598 (lit $N_D^{14.75}$ 1.5615).

K. U. Auwers, Justus Liebigs Ann.Chem., 442, 160 (1921).

EXAMPLE 17

Preparation of 4-chloro-o-toluidine

To a vigorously stirred solution of 1.10 grams (0.0059 mole) of 4-chloro-2(thiomethoxymethyl)aniline in 30 ml. of absolute ethanol cooled to 0° C. was added ca. 9 grams (3 teaspoons) of W-2 Raney Nickel. After stirring the mixture vigorously for 10 minutes, the Raney Nickel was removed by filtration, and washed twice with 50 ml of methylene chloride. The solvents were removed by rotatory evaporation. The resultant residue was taken up in 25 ml. methylene chloride and dried with magnesium sulfate. The drying agent was removed by filtration and washed with two 50-ml. portions of methylene chloride.

The solvents were removed at reduced pressure to yield 0.66 gram of a mixture of 4-chloro-o-toluidine and o-toluidine. This mixture was analyzed by vapor phase chromatography using a 10% Carbowax 20M:KOH on 60/80 "Chromsorb W" column at 150° C. which showed the mixture to be 90% 4-chloro-o-toluidine and 10% o-toluidine. The yield of 4-chloro-o-toluidine (0.594 gram, 0.0042 mole) is 72% and the yield of o-toluidine (0.066 gram, 0.00062 mole) is 10%.

EXAMPLE 18

Preparation of 2-methyl-6-(thiomethoxymethyl)aniline

To a rapidly stirred solution of 11.5 grams (0.11 mole) of o-toluidine in 400 ml. of methylene chloride cooled to −78° C. under nitrogen was added dropwise from a jacketed constant pressure addition funnel 11.7 grams (0.11 mole) of tert.-butyl hypochlorite at −78° C. This solution was stirred for 40 minutes during which time the solution turned dark green. The funnel was rinsed with methylene chloride, 25 ml. (ca. 3 equivalents) of dimethyl sulfide placed in the funnel and cooled. Upon dropwise addition of the sulfide, the solution turned dark red. After 1½ hours a voluminous white precipitate had formed; the reaction mixture was stirred for an additional 30 minutes. In the funnel was placed 7.0 grams (0.13 mole, 1.2 equivalent) of sodium methoxide dissolved in 50 ml. of methanol. This base was cooled and quickly added to the reaction mixture. The bath was allowed to come to room temperature overnight. The inorganic salts formed were removed by addition of 100 ml. of water. The heterogeneous mixture was separated; the aqueous layer was washed two times with 150-ml. portions of methylene chloride; the organic layers were combined, dried over anhydrous sodium sulfate, filtered, and concentrated on the rotary evaporator to yield a red oil. Fractionation of the resultant oil gave 1.80 grams (0.017 mole) of o-toluidine and 11.38 grams (0.068 mole) of 2-methyl-6-(thiomethoxymethyl)aniline for a 64% yield based on starting material and a 75% yield based on unrecovered starting material:

b.p. 82.5-84.5° C. (0.03 mm);
$N_D^{24.0}$ 1.5963 (lit. $N_D^1$ 1.5998). [1]See reference b) on page 1.

EXAMPLE 19

Preparation of 2-thiomethoxymethylaniline

A vigorously stirred solution of 10.0 grams (0.11 mole) of aniline in 250 ml. of methylene chloride was cooled to −78° C. under nitrogen. In a jacketed constant pressure addition funnel 11.7 grams (0.11 mole) of tert.-butyl hypochlorite was also cooled to −78° C. and added dropwise to the aniline solution over a 5-minute period. The stirring was continued for 25 additional minutes at which time the reaction mixture had turned dark green. The addition funnel was rinsed with a few ml. of methylene chloride and 25 ml. (ca. 30 equivalents) of dimethyl sulfide, was placed in the funnel and cooled to −78° C. Upon addition of the dimethyl sulfide an exotherm was observed; this solution was stirred for 40 minutes. In 50 ml. of methanol, 7.0 grams (0.13 mole, 1.2 equivalents) of sodium methoxide was placed in the funnel, cooled to −78° C., and quickly added to the reaction mixture. This solution was allowed to stir for one hour at −78° C. at which time 100 ml. of water were added and the heterogeneous mixture was allowed to come to room temperature. The layers were separated, the aqueous layer was extracted with two 100-ml. portions of methylene chloride, the combined organic extracts were washed with saturated sodium chloride, dried over anhydrous sodium sulfate, filtered, and the solvent was removed in vacuo to leave a dark red oil. This oil was fractionally distilled to yield 1.84 grams (0.02 mole) of aniline and 11.82 grams (0.077 mole) of 2-thiomethoxymethylaniline for a 72% yield based on starting material and 88% yield based on unrecovered starting material: b.p. 135°–139° C. (10 mm), $N_D^{24.0}$ 1.6083.

EXAMPLE 20

Preparation of 2-(2-tetrahydrothienyl)aniline

To a vigorously stirred solution of 10.0 grams (0.11 mole) of aniline in 200 ml. of methylene chloride cooled to −78° C. under nitrogen were added by means of a jacketed constant pressure additional funnel 11.7 grams (0.11 mole) of tert.-butyl hypochlorite also cooled to −78° C. This solution was stirred for 10 minutes. The funnel was rinsed with a few ml. of cold methylene chloride and 44 ml. (ca. 5 equivalents) of tetrahydrothiophene was cooled to −78° C., added dropwise to the reaction mixture, and stirred for three hours. In 50 ml. of methanol, 7.0 grams (0.13 mole, 1.2 equivalents) of sodium methoxide were placed in the funnel, cooled, and added quickly to the reaction mixture. The dry-ice/acetone cooling bath was removed and the solution stirred for 2 hours. The reaction was quenched by the addition of 100 ml. of water, the heterogeneous mixture separated, the aqueous layer was extracted two times with 100-ml. portions of methylene chloride. The combined organic layers were washed with saturated sodium chloride solution, dried over anhydrous sodium sulfate, and filtered. The solvent was removed in vacuo to produce a dark red oil. Fractional distillation of the oil gave 5.03 grams (0.054 mole) of aniline and 6.11 grams (0.034 mole) of 2-(2-tetrahydrothienyl)aniline for a 31% yield based on starting material and a 64% yield based on unrecovered starting material: b.p. 130°–134° C. (0.19 mm), $N_D^{26.8}$ 1.6258, IR (neat) 2.92, 3.36, 6.12, 6.70, and 13.40μ, NMR $(CCl_4)$T 7.82 (4H, m), 6.99 (2H, m) 6.06 (2H, s), 5.52 (2H, t), 3.20 (4H, m).

Anal. Calculated for $C_{10}H_{13}NS$: C, 66.99; H, 7.31; N, 7.81; S, 17.88. Found: C, 67.04; H, 7.29; N, 7.74.

EXAMPLE 21

Preparation of 2-methyl-6-(thiomethoxymethyl)aniline

To a rapidly stirred solution of 11.5 grams (0.11 mole) of o-toluidine in 400 ml. of methylene chloride cooled to −78° C. under nitrogen was added dropwise from a jacketed constant pressure addition funnel 11.7 grams (0.11 mole) of tert.-butyl hypochlorite at −78° C. This solution was stirred for 40 minutes during which time the solution turned dark green. The funnel was rinsed with methylene chloride, 25 ml. (ca. 3 equivalents) of dimethyl sulfide placed in the funnel and cooled. Upon dropwise addition of the sulfide, the solution turned dark red. After 1½ hours a voluminous white precipitate had formed, the reaction mixture was stirred for an additional 30 minutes. In the funnel were placed 7.0 grams (0.13 mole, 1.2 equivalents) of sodium methoxide dissolved in 50 ml. of methanol. This base was cooled and quickly added to the reaction mixture. The bath was allowed to come to room temperature overnight. The inorganic salts formed were removed by addition of 100 ml. of water. The heterogeneous mixture was separated, the aqueous layer was washed two times with 150-ml. portions of methylene chloride, the organic layers were combined, dried over anhydrous sodium sulfate, filtered, and concentrated on the rotary evaporator to yield a red oil. Fractionation of the resultant oil gave 1.80 grams (0.017 mole) of o-toluidine and 11.38 grams (0.068 mole) of 2-methyl-6-(thiomethoxymethyl)aniline for a 64% yield based on starting material and a 75% yield based on unrecovered starting material: b.p. 82.5°–84.5° C. (0.03 mm), $N_D^{24.0}$ 1.5963 (lit[1] $N_D$ 1.5998).

[1]See reference b) on page 1.

EXAMPLE 22

Preparation of 4-chloro-2-(thiomethoxymethyl)aniline

In 150 ml. of methylene chloride, 5.50 grams (0.043 mole) of p-chloroaniline were dissolved and cooled to −78° C. under nitrogen. In a jacketed constant pressure addition funnel 4.67 grams (0.043 mole) of tert.-butyl hypochlorite in 10 ml. of methylene chloride were cooled to −78° C. and added dropwise to the aniline solution. The reaction mixture was stirred for 30 minutes, during which time the solution turned dark yellow. The funnel was rinsed with 15 ml. of methylene chloride; 25 ml. (ca. 5 equivalents) of dimethyl sulfide was placed in the funnel and cooled to −78° C. The sulfide was added dropwise and the reaction stirred for 5½ hours. To the reaction mixture were added 7.00 grams (0.052 mole, 1.2 equivalents) of sodium methoxide in 50 ml. of methanol. The resultant solution was stirred for 1 hour at −78° C., the bath was removed, the reaction mixture was allowed to warm to room temperature overnight. The reaction was quenched by addition of 100 ml. of water, the layers were separated, the aqueous phase was extracted two times with 150 ml. of methylene chloride. The combined organic extracts were washed with saturated sodium chloride solution, dried over anhydrous sodium sulfate, filtered, and the solvent evaporated to yield a red solid. Chromatography on silica gel (25% ether-pentane solvent) separated the product from starting material. The first compound eluted was 4-chloro-2thiomethoxymethylaniline (5.44 grams, 0.029 mole, 67%, 90% based on recovered starting material). M.p. 79°–80° C. (lit.[1] m.p. 78°–79° C). The remaining 1.85 grams of material eluted was a mixture of product and starting material.

[1] lit reference: See reference (b) on page 1.

EXAMPLE 23

Preparation of 3-methyl-2-(thiomethoxymethyl)aniline and 5-methyl-2-(thiomethoxymethyl)aniline To a vigorously stirred solution of 11.5 grams (0.11 mole) of m-toluidine in 400 ml. of methylene chloride cooled to −78° C. under nitrogen were added dropwise 11.7 grams (0.11 mole) of tert.-butyl hypochlorite in 10 ml. of methylene chloride (also cooled to −78° C. in a jacketed constant pressure addition funnel). The solution turned red and was stirred for 30 minutes. The funnel was rinsed with 15 ml. of methylene chloride and 25 ml. (ca. 31 equivalents) of dimethyl sulfide was cooled to −78° C., added dropwise to the reaction mixture, and stirred for 3 hours. A solution of 7.0 grams (0.13 mole, 1.2 equivalents) of sodium methoxide in 50 ml. of methanol was cooled in the funnel and added quickly to the reaction mixture. The dry-ice/acetone bath was allowed to warm to room temperature overnight. The reaction was quenched with 100 ml. of water, the heterogeneous mixture was separated, and the aqueous layer was extracted twice with 150-ml. portions of methylene chloride. The combined organic layers were washed with saturated sodium chloride solution, dried over anhydrous sodium sulfate, filtered, and concentrated on the rotary evaporator to yield a dark purple oil. Fractionation of the resultant oil gave 4.85 grams (0.045 mole) of m-toluidine and 9.40 grams (0.056 mole) of an approximately 1:1 mixture of the two named products for a 50% yield based upon starting material and 90% yield based upon unrecovered starting material: b.p. 87°–90° C. (0.06 mm).

EXAMPLE 24

Preparation of 3-chloro-2-(thiomethoxymethyl)aniline and 5-chloro-2-(thiomethoxymethyl)aniline A solution of 13.7 grams (0.11 mole) of m-chloroaniline in 400 ml. of methylene chloride was vigorously stirred and cooled to −78° C. under nitrogen. To this solution from a jacketed constant pressure addition funnel were added 11.7 grams (0.11 mole) of tert.-butyl hypochlorite at −78° C. The dropwise addition required five minutes and the reaction mixture was stirred an additional 35 minutes. The funnel was washed with 15 ml. of cold methylene chloride and 25 ml. (ca. 3 equivalents) of dimethyl sulfide placed in it. The sulfide was added dropwise and the solution stirred for six hours. A solution of 7.0 grams (0.13 mole, 1.2 equivalents) of sodium methoxide in 50 ml. of methanol was cooled in the funnel and quickly added to the reaction mixture. The dry-ice/acetone bath was allowed to warm to room temperature overnight. The inorganic salts formed were hydrolyzed by the addition of 100 ml. of water, the layers separated, and the aqueous phase washed with two 150-ml. portions of methylene chloride. The combined organic layers were dried over anhydrous sodium sulfate, filtered, and the solvents evaporated to produce a dark purple oil. The oil was fractionally distilled to yield 6.98 grams (0.055 mole) of 3-chloro-aniline and 9.99 grams (0.053 mole) of an approximately 60:40 mixture of 3-chloro-2-(thiomethoxymethyl)aniline and 5-chloro-2-(thiomethoxymethyl)aniline for a 50% yield based on starting material and a 87% yield based on unrecovered starting material: b.p. 128°–130° C. (0.08 mm), $N_D^{23.7}$ 1.6196 (lit. $N_D$ 1.6205).

EXAMPLE 25

Preparation of 2-amino-3-n-butylpyridine

To a stirred solution of 2-aminopyridine (4.7 g, 0.05 mole) in 100 ml. of methylene chloride at −65° C. was added dropwise a solution of t-butyl hypochlorite (5.43 g, 0.05 mole) in 10 ml. of methylene chloride cooled in a dry-ice/acetone bath. The reaction mixture was stirred for 1 hour. Tetrahydrothiophene (4.4 g, 0.05 mole) in 10 ml. of methylene chloride cooled in a dry-ice/acetone bath was introduced and stirred for 4 hours. Then sodium methoxide (3.43 g, 0.063 mole) in 30 ml. of absolute methanol cooled in a dry-ice/acetone bath was added and the resulting solution was stirred about 1–2 hours and allowed to warm up to room temperature. Work-up in the usual manner gave a crude residue (8.87 g, ∼ 100%) which was mixed with potassium t-butoxide (5.60 g, 0.05 mole) in 250 ml. of t-butyl alcohol and refluxed for 22 hours. After cooling to room temperature, water was added and the aqueous layer was extracted with ether. The combined ethereal extracts were concentrated to a residual oil which was taken up in methylene chloride and dried over anhydrous sodium sulfate. The sodium sulfate was removed by filtration and the solvent was distilled to give the dark brown oily sulfide (7.34 g). Chromatography on silica gel (Skelly Solve B-ethyl acetate) gave an orange-red oil (3.03 g) whose NMR spectrum showed a small amount of impurity. The oily sulfide was mixed with Raney Nickel (W-2, about 80 g. suspended in absolute ethanol) in 120 ml. of absolute ethanol and vigorously stirred for 3.5 hours at room temperature. Work-up in usual manner gave an oily 3-n-butyl-2-aminopyridine (1.99 g) which was chromatographed on silica gel (Skelly Solve B-ethyl acetate) to give crystalline material (0.75 g, 10%), m.p. 45.6°–47.0° C. Further recrystallization from pentane gave an analytical sample, m.p. 48°–49° C.; NMR (CDCl$_3$) δ0.66–1.92 (broad multiplet, 7H), 2.16–2.58 (broad multiplet, 2H), 2.46 (broad singlet, 2H), 6.54 (d of d, 1H), 7.25 (d of d, 1H), and 7.95 (d of d, 1H).

Exact Mass Molecular Weight.

Calculated for $C_9H_{14}N_2$: 150.1156 Found: 150.1159

In a manner similar to that described above, N-chloro-4-aminopyridine is prepared and reacted with dimethylsulfide to form the azasulfoniumchloride salt, which is then reacted with sodium methoxide, and the reaction mixture is worked up to form 3thiomethoxymethyl-4-aminopyridine, which can also be named 3-methylthiomethyl-4-aminopyridine. This thio-ether can be reduced with Raney Nickel, by procedures exemplified above to prepare 3-methyl-4-aminopyridine, which is useful as an intermediate in making azo-dyes, e.g., by diazotization with nitrous acid to form a diazonium salt which is then coupled with a phenol such as B-naphthol to form an azo-dye.

EXAMPLE 26

Preparation of 2-amino-3,4-dimethylpyridine

To a stirred solution of 2-amino-4-methylpyridine (4.32 g, 0.04 mole) in 100 ml. of methylene chloride at −65° C. was added dropwise a solution of t-butyl hypochlorite (4.36 g, 0.04 mole) in 15 ml. of methylene chloride cooled in a dry-ice/acetone bath. The resulting solution was further stirred for 1-1/5 hours. Dimethyl sulfide (5 ml., 0.068 mole) in 10 ml. of methylene chloride cooled in a dry-ice/acetone bath was introduced and stirred for 1 hour. Sodium methoxide (2.8 g, 0.052 mole) in 25 ml. of absolute methanol cooled in a dry-ice/acetone bath was added and stirred for 2 and ¼ hours to form a reddish black oil (8.60 g.) which was mixed with potassium t-butoxide (4.5 g., 0.04 mole) in 200 ml. of t-butyl alcohol and refluxed for 19 hours. Work-up in the usual manner gave a reddish-brown oil (7.22 g.) which was primarily 2-amino-3-(thiomethoxymethyl)-4-methylpyridine.

The reddish oil was mixed with 135 g. of a suspension of Raney Nickel (W-2, suspended in absolute ethanol) in 150 ml. of absolute ethanol and vigorously stirred for 2 hours. Desulfurization was shown to be complete by a thin layer chromatography. The Raney Nickel was filtered off and washed with four 70 ml. portions of ethanol. The combined ethanol extracts were concentrated to give an oil which was dissolved in methylene chloride and dried over anhydrous magnesium sulfate. The drying agent was filtered off and the solvent was removed on a rotatory evaporator to give a light yellow solid (1.53 g., 31.4%) which was chromatographed on silica gel (Skelly Solve B-ethyl acetate) to give 2-amino-3,4-dimethyl pyridine whose NMR spectrum showed some impurity due to 2-amino-4-methylpyridine. Further recrystallization from cyclohexane gave a light yellow crystal (0.83 g., 17%), m.p. 79.5°–81° C. Further recrystallization from the above solvent gave a sample, m.p. 81.5°–82° C. (lit. describes the compound as a low melting solid); NMR (CDCl$_3$) δ1.97 (s, 3H), 2.06 (s, 3H), 4.86 (broad s, 2H), 6.42 (d, 1H, J=5 Hz), and 7.46 (d, 1H, J=5 Hz).

Exact Mass Molecular Weight.

Calculated for C$_7$H$_{10}$N$_2$: 122.0843 Found: 122.0846

M.p. of 2-amino-3,4-dimethylpyridine hydrochloride: 251°–252° (decomp.) (lit.[1] m.p. 239°–240° ).

1. A. Albert and R. E. Willette, *J. Chem. Soc.*, 4063 (1964).

In a manner similar to that described above, 3-amino-4-methylpyridine can be converted to its N-chloro-3-amino-4-methylpyridine and reacted with dimethylsulfide to form the azasulfonium chloride salt. This salt can be treated with base to form the 3-amino-2-thiomethoxymethyl-4-methylpyridine thio-ether. This thioether can be reduced with Raney Nickel to form the 3-amino-2,4-dimethylpyridine.

EXAMPLE 27

Preparation of 2-amino-5-methyldiphenylthiophenoxymethane

To a rapidly stirred solution of 2.7 g. (0.025 mole) of p-methylaniline and 16.0 g. (0.080 mole) of benzylphenylsulfide in 300 ml. of dry acetonitrile and 100 ml. of methylene chloride under nitrogen at −40° C., was added dropwise 3.5 g. (0.032 mole, 28% excess) of t-butylhypochlorite in 25 ml. of methylene chloride at −78° C. in diffuse light. The reaction mixture was stirred 4 hours at −40° C., then allowed to warm slowly to −20° C. over 3 hours. Sodium methoxide (7.0 g, 0.13 mole) in 50 ml. of methanol at 25° C. was added quickly. The reactive mixture was stirred for 1 hour as it warmed to room temperature. The solution was concentrated in vacuo, 250 ml. of dry toluene and 30 ml. of triethylamine were added, and the solution heated under reflux for 12 hours. The solution was concentrated in vacuo, 100 ml. of water was added, and the product was extracted with five 100-ml. portions of methylene chloride. The combined organic phases were washed with 50 ml. of 5% aqueous sodium hydroxide, 100 ml. of saturated sodium chloride solution, dried over anhydrous magnesium sulfate, and filtered. The solvent was removed in vacuo leaving an orange oil which was chromatographed on 400 g. of Fisher basic alumina (Act I) using ether-pentane as eluant. Recovered was 5.7 g. (73% based on p-methylaniline) of 2-amino-5-methyldiphenlthiophenoxymethane as a yellow oil: ir (cm$^{-1}$)(CCl$_4$) 3480, 3380, 3050, 1630, 1580, 1490, 1450, 1270, 1150, 1080, 1020; NMR (CCl$_4$) τL 2.4–3.7 (13H, m), 4.46 (1H, s), 6.15–6.4 (2H, br s), 7.85 (3H, s); mass spectrum m/e 305(4), 196(100), 180 (12). The corresponding p-nitrobenzamide was prepared from the aminosulfide and p-nitrobenzoyl chloride, m.p. 156°–157° C; ir (cm$^{-1}$) (KBr) 3350, 3090, 1670, 1600, 1500, 1440, 1380, 1100, 1020, 848, 815, 763, 746, 703, 691; NMR (CDCl$_3$) τ: 1.2–3.2 (18H, m), 4.34 (1H, s), 7.75 (3H, s); mass spectrum m/e 454(1), 345(100), 218(4), 194(32), 150(12).

EXAMPLE 28

Preparation of 2-aminodiphenylthiophenoxymethane

To a rapidly stirred solution of 2.3 g. (0.025 mole) of aniline and 10.0 g (0.050 mole) of benzylphenylsulfide in 300 ml. of dry acetonitrile and 100 ml. of methylene chloride under nitrogen at −40° C., was added dropwise 3.5 g. (0.032 mole, 28% excess) of tert-butylhypochlorite in 25 ml. of methylene chloride at −78° C. in diffuse light. The reaction mixture was stirred 4 hours at −40° C. then allowed to warm slowly to −20° C. over 3 hours. Sodium methoxide (7.0 g., 0.13 mole) in 50 ml. of dry methanol (at 25°) was added quickly. The reaction mixture was stirred for 1 hour as it warmed to room temperature. The solution was concentrated in vacuo, 100 ml. of water was added, and extracted with 5 × 100 ml. of chloroform. The combined organic phases were washed with 50 ml of 5% aqueous sodium hydroxide, 100 ml. of saturated sodium chloride solution, dried over anhydrous magnesium sulfate, and filtered. Solvent was removed in vacuo giving a dark brown oil which was chromatographed on 300 g. of Fisher basic alumina (Act I) using etherpentane as eluant. Recovered was 5.2 g. (72% yield based on starting aniline) of 2-aminodiphenylthiophenoxymethane. Recrystallizaton from ethanol-water gave light yellow crystals, m.p. 64°–65.50°; ir (cm$^{-1}$) (CCl$_4$) 3480, 3380, 3090, 1620, 1580, 1490, 1450, 1310, 1270, 1160, 1080, 1070, 1025, 690; NMR (CCl$_4$) τ: 2.4–3.7 (14H, m), 4.51 (1H, s), 6.0–6.4 (2H, br s).

Anal. Calculated for C$_{19}$H$_{17}$NS: C, 78.31; H, 5.88; N, 4.81. Found: C, 78.28; H, 5.85; N, 4.88.

EXAMPLE 29

Preparation of 2-amino-5-chlorodiphenylthiophenoxymethane

To a rapidly stirred solution of 3.2 g. (0.025 mole) of para-chloroaniline and 16.0 g. (0.080 mole) of benzylphenylsulfide in 300 ml. of dry acetonitrile and 100 ml. of methylene chloride under nitrogen at −40° C. was added dropwise 3.5 g. (0.032 mole, 28% excess) of tert-butylhypochlorite in 25 ml. of methylene chloride at −78° C. in diffuse light. The reaction mixture was stirred 4 hours at −40° C. then allowed to warm slowly to −20° C. over 3 hours. Sodium methoxide (7.0 g., 0.13 mole) in 50 ml. methanol at 25° C. was added quickly. The reaction mixture was stirred for 1 hour as it warmed to room temperature. The solution was concentrated in vacuo, 250 ml. of dry toluene and 15 ml. of triethylamine were added, and the solution was heated under reflux for 12 hours. The solution was concentrated in vacuo, 100 ml. of water was added, and product was extracted with five 100-ml. portions of methylene chloride. The combined organic phases were washed with 50 ml. of 5% aqueous sodium hydoxide, 100 ml. of saturated sodium chloride solution, dried over anhydrous magnesium sulfate, and filtered. Solvent was removed in vacuo leaving a yellow oil which was chromatographed on 400 g. of Fisher basic alumina (Act I) using ether-pentane as eluant. Recovered was 7.6 g. (94% based on para-chloroaniline of 2-amino-5-chlorodiphenylthiophenoxymethane as light yellow oil, ir (cm$^{-1}$) (CCl$_4$) 3480, 3380, 3090, 1620, 1580, 1480, 1450, 1410, 1280; NMR (CCl$_4$) τ: 2.5–3.7 (13H, m), 4.61 (1H, s), 6.15–6.40 (2H, br s); mass spectrum m/e 325, 216 (100). The corresponding p-nitrobenzamide was prepared from the aminosulfide and p-nitrobenzoyl chloride, m.p. 159°–161° C.; ir (cm$^{-1}$) (KBr) 3350, 3090, 1670, 1600, 1500, 1390, 1340, 1280, 1110, 850, 815, 748, 712, 692; NMR (CDCl$_3$) τ: 1.2–3.0 (18H, m), 4.38 (1H, s); mass spectrum m/e 474(1), 365(100), 212(34), 150(36).

EXAMPLE 30

Preparation of 2-amino-5-nitrodiphenylthiophenoxymethane

To a rapidly stirred solution of 3.5 g. (0.025 mole) of p-nitroaniline and 10.0 g (0.050 mole) of benzylphenylsulfide in 300 ml. of dry acetonitrile and 100 ml of methylene chloride under nitrogen at −40° C. was added dropwise 3.5 g. (0.032 mole, 28% excess) t-butylhypochlorite in 25 ml. of methylene chloride at −78° C. in diffuse light. The reaction mixture was stirred for 4 hours at −40° C., then allowed to warm slowly to −20° C. over 3 hours. Sodium methoxide (7.0 g., 0.13 mole) in 50 ml. of methanol at 25° C. was added quickly. The reaction mixture was stirred for 1 hour as it warmed to room temperature. The solution was concentrated in vacuo, 250 ml. of dry toluene and 30 ml. of triethylamine were added, and the solution was heated under reflux for 36 hours. The solution was concentrated in vacuo, 100 ml. of water was added, and product was extracted with five 100-ml. portions of methylene chloride. The combined organic phases were washed with 50 ml. of 5% aqueous sodium hydroxide, 100 ml. of saturated sodium chloride solution, dried over anhydrous magnesium sulfate, and filtered. Solvent was removed in vacuo leaving an orange oil which was chromatographed on 400 g. of Fisher basic alumina (Act I) using ether as eluant. Recovered was 5.5 g. (65% based on p-nitroaniline) of 2-amino-5-nitrodiphenylthiophenoxymethane as yellow crystals m.p. 103°–105° C.; ir (cm$^{-1}$) (KBr) 3480, 3380, 3050, 1620, 1570, 1480, 1380, 1150, 1090, 905, 825, 745, 725, 695; NMR (CDCl$_3$) τ: 1.8–3.5 (13H, m), 4.50 (1H, s), 5.2–5.4 (2H, br s); mass spectrum m/e 336(1), 227(100), 180(35).

By replacing the amino pyridine of Example 26 with other amino pyridines indicated below, ortho-thio-ether amino pyridine compounds can be prepared by using the desired sulfide reactant followed by base treatment in the above-described process. With some amino-pyridines, mixtures of ortho-thio-ether amino pyridines will be obtained where two alternate ortho positions, relative to the amino nitrogen are present. Examples of new compounds which can be prepared according to this invention include:

2-amino-3-(2-thiacyclobutyl)pyridine,
N-methyl-2-amino-4-nitro-3-thioethoxyethylpyridine,
2-amino-3-thiomethoxymethylpyridine,
2-amino-4-chloro-3-thiomethoxymethylpyridine,
2-amino-4-acetoxy-3-thiomethoxymethylpyridine,
N-methyl-2-amino-3-carbonyloxyphenyl-4-thioethoxyethylpyridine,
N-methyl-2-amino-4,5-dichloro-3-thiohexyloxyhexylpyridine,
2-amino-4-methoxy-5-chloro-3-thiomethoxymethylpyridine,
2,4-diamino-3-thiomethoxymethylpyridine,
N-t-butyl-3-amino-2-thiopropyloxypropylpyridine,
N-methyl-3-amino-2-methyl-4-thiobutoxybutylpyridine,
3-amino-4-(2-pentahydrothiaphenyl)pyridine,
3-amino-4-carbonyloxypentyl-2-thiomethoxymethylpyridine,
3,5-diamino-4-thiophenoxybenzylpyridine,
3-amino-5-propionoxy-4-thiomethoxymethylpyridine,
4-amino-3-methyl-5-thiophenoxybenzylpyridine,
4-amino-2-ethoxy-3-thiomethoxymethylpyridine,
4-amino-3-carbonyloxyethyl-5-(2-tetrahydrothienyl)-pyridine.
4-amino-2-fluoro-5-thiomethoxymethylpyridine,
4-amino-3-bromo-5-thiophenoxybenzylpyridine, and the like.

The new compounds provided by this invention, then include those of the formula:

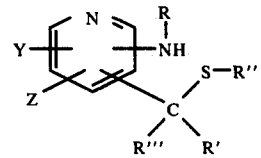

wherein R is a hydrogen or hydrocarbon radical free of aliphatic unsaturation containing from 1 to 8 carbon atoms; the —N(R)H group is in a position ortho, meta, or para to the pyridine ring nitrogen; and the thio-ether group is ortho to —N(R)H; each of Y and Z is hydrogen, halogen, nitro, cyano, amino, lower alkyl, lower alkyloxy, lower acyloxy, carbonyloxyl-lower alkyl or carbonyloxy-phenyl; R′ is hydrogen, lower alkyl or phenyl; R″, taken separately, is lower alkyl or phenyl; R‴, taken separately, is hydrogen, lower alkyl or phenyl; and R″ and R‴, when taken together with the

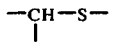

moiety denote a ring containing 3 to 5 methylene carbon atoms.

Preferred compounds are those wherein each of Y and Z is hydrogen, halogen, or lower alkyl, and R is hydrogen, R' is hydrogen, R" is lower alkyl, and R''' is hydrogen. Most preferably Y and Z are both hydrogen.

It is to be understood that the invention is not to be limited to the exact details of operation or exact compounds, reaction mixtures, methods or procedures shown and described, as obvious modifications and equivalents will be apparent to one skilled in the art.

We claim:

1. A compound of the formula:

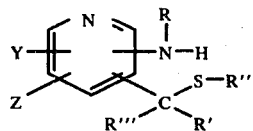

wherein R is hydrogen or hydrocarbon radical free of aliphatic unsaturation containing from 1 to 8 carbon atoms; the —N(R)H group is in a position ortho, meta or para to the pyridine ring nitrogen; wherein one of Y and Z is hydrogen, halogen, nitro, cyano, amino, lower-alkylamino, lower-alkyl, lower-alkyloxy, lower-alkanoyloxy, a carbonyloxy-lower alkyl or carbonyloxy-phenyl; and wherein the other one of Y and Z is hydrogen, or wherein both Y and Z are simultaneously halogen, or wherein one of Y and Z is lower-alkoxy and the other one of Y and Z is halogen; R' is hydrogen, lower-alkyl or phenyl; R", taken separately, is lower-alkyl or phenyl; R''', taken separately, is hydrogen, lower-alkyl or phenyl; no more than two of R', R", and R''' being lower-alkyl at any one time, no more than two of R', R", and R''' being phenyl at any one time; and wherein R" and R''', when taken together with the

moiety denote a ring containing 3 to 5 methylene carbon atoms and the hydrocarbon-S-hydrocarbyl thioether group is attached ortho to the N(-R)H group.

2. A compound as defined in claim 1 wherein each of Y and Z is hydrogen, R is hydrogen, R' is hydrogen, R" is lower alkyl, and R''' is hydrogen.

3. A compound as defined in claim 2 wherein the compound is 3-(thiomethoxymethyl)-2-aminopyridine.

4. A compound as defined in claim 1 wherein Y is hydrogen, Z is lower alkyl, R is hydrogen, R' is hydrogen, R" is lower alkyl, and R''' is hydrogen.

5. A compound as defined in claim 4 wherein the compound is 2-amino-3-(thiomethoxymethyl)-4-methyl-pyridine.

* * * * *

UNITED STATES PATENT OFFICE
CERTIFICATE OF CORRECTION

Patent No. 4,035,375                     Dated    July 12, 1977

Inventor(s)   Paul G. Gassman and Gordon D. Gruetzmacher

It is certified that error appears in the above-identified patent and that said Letters Patent are hereby corrected as shown below:

Col. 5, line 17; "effect" should read --affect--
Col. 5, line 53; "compound" should read --compounds--
Col. 6, line 32; "week" should read --weed--
Col. 7, line 26; "temperatures" should read --temperature--
Col. 7, line 62; "mole" should read --mole)--
Col. 9, line 60; "Yield" should read --yield--
Col. 10, line 15; "aniline" should read --anilino--
Col. 12, line 55; "organiclayers" should read --organic layers--
Col. 18, line 59-60; "3thiomethoxymethyl" should read -- 3-thiomethoxymethyl--
Col. 20, line 58; "etherpentane" should read --ether-pentane--

Signed and Sealed this

Twenty-eighth Day of March 1978

[SEAL]

Attest:

RUTH C. MASON
Attesting Officer

LUTRELLE F. PARKER
Acting Commissioner of Patents and Trademarks